(12) United States Patent
Dalmia et al.

(10) Patent No.: US 6,259,109 B1
(45) Date of Patent: Jul. 10, 2001

(54) WEB INSPECTION SYSTEM FOR ANALYSIS OF MOVING WEBS

(75) Inventors: Arun Dalmia, Peabody, MA (US); Conor O'Neill, Clonmel (IE); Anthony W. Wilson, Stoneham; David M. Simmons, Peabody, both of MA (US)

(73) Assignee: Datacube, Inc., Danvers, MA (US)

( * ) Notice: Subject to any disclaimer, the term of this patent is extended or adjusted under 35 U.S.C. 154(b) by 0 days.

(21) Appl. No.: 09/137,789

(22) Filed: Aug. 21, 1998

Related U.S. Application Data

(60) Provisional application No. 60/057,707, filed on Aug. 27, 1997.

(51) Int. Cl.$^7$ .......................... G01N 21/86; G01N 21/88
(52) U.S. Cl. ............................... 250/559.08; 250/559.07; 356/429
(58) Field of Search .................... 250/559.07, 559.08, 250/559.44, 559.45, 559.46; 356/429, 430, 237.1, 239.3; 348/125, 128, 88; 382/108

(56) References Cited

U.S. PATENT DOCUMENTS

| | | | |
|---|---|---|---|
| 4,417,149 | * 11/1983 | Takeuchi et al. | 250/559.46 |
| 4,824,209 | * 4/1989 | Bolton et al. | 362/31 |
| 5,440,648 | * 8/1995 | Roberts et al. | 356/430 |
| 5,870,203 | * 2/1999 | Chiu et al. | 250/559.46 |
| 5,945,988 | * 8/1999 | Williams et al. | 345/327 |

\* cited by examiner

*Primary Examiner*—John R. Lee
*Assistant Examiner*—Kevin Pyo
(74) *Attorney, Agent, or Firm*—Weingarten, Schurgin, Gagnebin & Hayes LLP

(57) ABSTRACT

A web inspection system for analysis of a moving web of material records and stores continuous sequences of the web. The web inspection system includes a camera for recording the continuous sequence of the web, an encoder for synchronizing movements of the web with the video image being recorded, and an Image Processing System (IPS) including a real time video disk for storing the image of the web and for displaying the continuous sequence web image on a video display. The IPS is also utilized for detecting faults or features and for categorizing the faults or features detected. The entire web is recorded and the image can be viewed either interactively while the image is being recorded or at a later time. The recorded image of the web can be played back at a slower speed to allow for a more detailed inspection of the web. The sequence image can be analyzed to build a defect image database. The web inspection system can also be utilized for sorting and displaying defect information.

25 Claims, 2 Drawing Sheets

WEB INSPECTION SYSTEM FOR ANALYSIS OF MOVING WEBS

CROSS REFERENCE TO RELATED APPLICATIONS

This application claims priority under 35 U.S.C. §119(e) to Provisional Patent Application serial No. 60/057,707, filed Aug. 27, 1997; the disclosure of which is incorporated herein by reference.

STATEMENT REGARDING FEDERALLY SPONSORED RESEARCH OR DEVELOPMENT

Not Applicable

BACKGROUND OF THE INVENTION

Moving webs of material such as films, paper, metals and textiles are extremely difficult to inspect with the naked eye. Typically the web of material is moving at a rate which is too fast for a human to efficiently and accurately analyze or inspect. The entire web of material must be inspected for faults or features since faults or features may occur at any location along the web. Faults or features include holes, spots, dirt, streaks, dents (three dimensional defects), coating and formation problems some of which may be as small as twenty five microns in size. Prior web inspection systems saved single images of web defects in a memory, but were not capable of recording the web continuously. It would be desirable to have a web inspection system which records continuous sequences of the web such that the web may be inspected interactively or at a later time. Additionally, when the web is viewed at a later time, it may be viewed at a slower rate, thus making the inspection of the web easier.

BRIEF SUMMARY OF THE INVENTION

A web inspection system for analysis of a moving web of material records and stores continuous sequences of the web. The web inspection system includes a camera for recording the continuous sequence of the web, an encoder for synchronizing movements of the web with the video image being recorded, and an Image Processing System (IPS) including a real time video disk for storing the image of the web and for displaying the continuous sequence web image on a video display. The IPS is also utilized for detecting faults or features and for categorizing the faults or features detected. The entire web is recorded and the image can be viewed either interactively while the image is being recorded or at a later time. The recorded image of the web can be played back at a slower speed to allow for easier inspection of the web. The sequence image can be analyzed to build a defect/feature image database. The web inspection system can also be utilized for sorting and displaying defect information.

BRIEF DESCRIPTION OF THE SEVERAL VIEWS OF THE DRAWING

The invention will be more fully understood from the following detailed description taken in conjunction with the accompanying drawings in which.

DETAILED DESCRIPTION OF THE INVENTION

Figure 1:
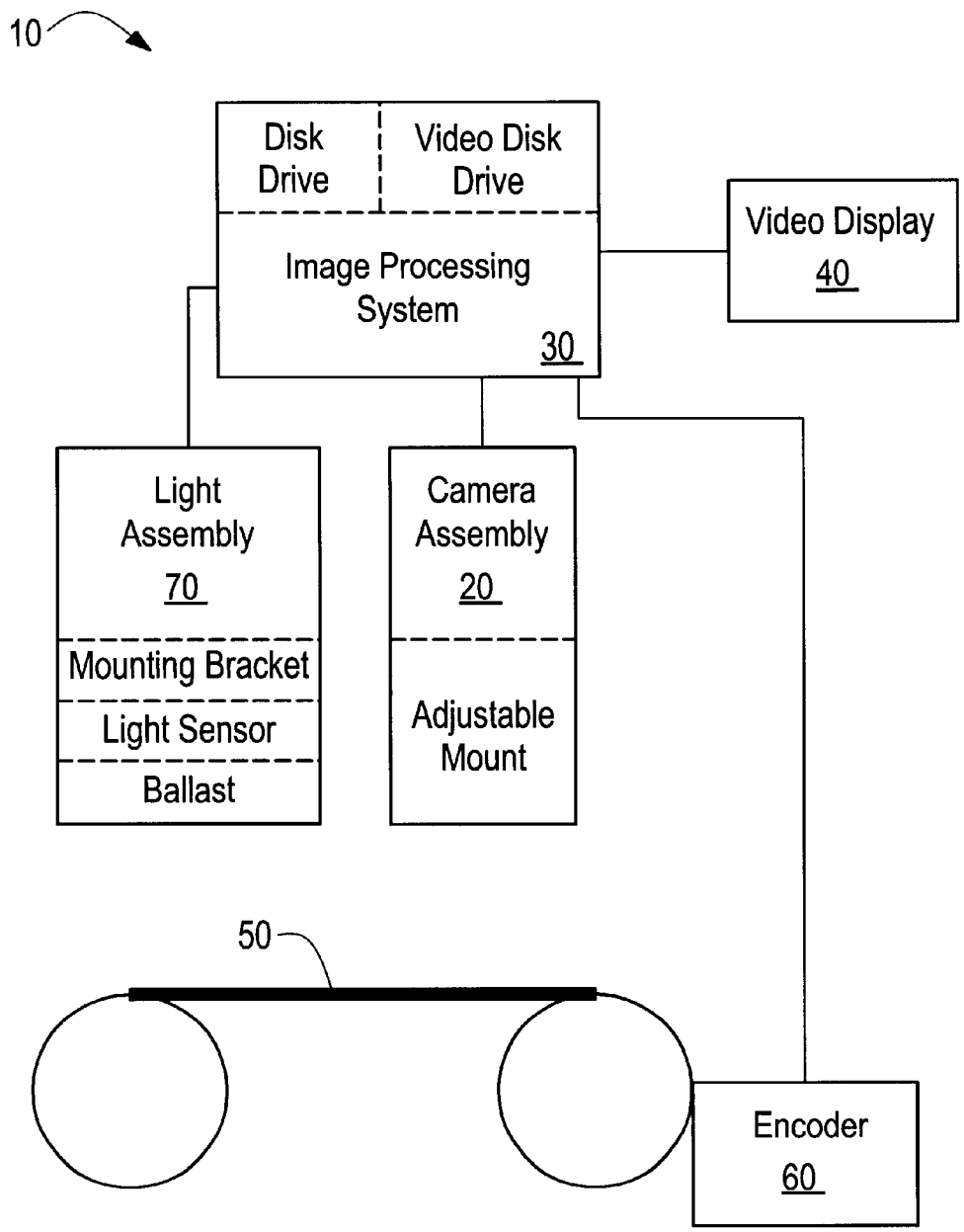
FIG. 1 is a block diagram of the web inspection system of the present invention.

Referring to FIG. 1 a web inspection system 10 for analysis of moving webs of material is shown. The web inspection system 10 includes a camera assembly 20, an image processing system 30, a video display 40 an encoder 60 and a light assembly 70 for inspecting the web of material 50.

The camera assembly 20 includes a rugged industrial enclosure, at least one camera such as a single linear array camera or an area camera for recording a sequence of images of the moving web of material, adjustable mounting brackets for securing the camera into an appropriate setting, an encoder interface and a light control interface. The camera mounts secure the camera in position and allow adjustments of the camera. The camera can be rotated, angularly adjusted along any axis and include minimal up and down adjustment. The camera mounts further act as heatsinks, dissipating heat away from the camera.

The camera assembly 20 is mounted solidly over the web 50 such that vibration or other unintended movements of the camera are eliminated or minimized. The camera assembly 20 should not be mounted near or downstream from dancer rolls or where the web 50 is susceptible to wander or flutter. Care should also be taken not to mount the camera assembly 20 where overhead lights may interfere with the proper illumination of the web 50.

The camera assembly 20 is preferably mounted to obtain the desired field of view for a given application. The angle of the camera(s) with respect to the web should enable the optimal imaging of the defects within the web. The distance between the camera assembly 20 and the web 50 should be optimized dependent upon the particular application. An example of how the distance between the camera and web is determined is described below.

First the resolution required to meet the demands of the inspection application are determined. Typically, the resolution can be estimated to be one half the size of the smallest defect requiring detection. If the minimum defect size is 1 mm, then the required resolution would be 0.5 mm.

Next, the field of view (the width of the web that is being imaged) is determined according to the following formula:

field of view=camera size in pixels×resolution 1024 pixels×0.05 mm=512 mm

Then the magnification is determined according to this formula:

magnification=field of view/camera sensor width 512 mm/13.3 mm=38.5

Then the distance from the camera lens to the web, known as the working distance, is calculated according to the formula:

working distance=magnification×focal length of lens 38.5×0.05= 1.925 m

Thus, in this example the distance between the camera and the web should be 1.925 meters.

In a particular embodiment a Dalsa high-speed line scan camera, model CL-C3, available from Dalsa in Ontario, Canada, is used to record a continuous sequence of images of the web of material being inspected. This camera has a 15 MHz clock and a resolution of 256 to 2048×1 (14 micrometers square pixels). A Nikon Nikkor 28 mm f/2 lens having a distance scale of 0.25 m to infinity is used with the Dalsa camera. Lens aperture settings can be automatically controlled by the camera. The encoder interface allows adjustment of the exposure control of the camera with respect to the speed of the moving web of material. The light interface adjusts camera settings with respect to the intensity of the light.

The Image Processing System (IPS) 30 is in electrical communication with the camera assembly 20, the encoder 60, the video display 40 and the light assembly 70. The IPS 30 includes a computer and a mass storage device such as a video disk for storing the continuous sequence of images of the moving web of material recorded by the camera. The recorded continuous sequence of images may be viewed interactively or at a later time on the video display 40. Additionally, the continuous sequence of images of the moving web may be viewed at a slower speed than the web was moving at thus allowing a more detailed inspection of the web.

The IPS 30, under program control, can identify and classify defects and save defect data. The inspection system 10 capabilities further include locating defects such as holes, spots, dirt, streaks, coating and formation problems; sorting and displaying useful defect information, as well as the displaying of real-time video of the web. The IPS 30 controls the camera, processes encoder information and controls the lighting.

The web inspection system 10 utilizes an encoder 60 to synchronize the IPS 30 to the movement of the web 50. In a particular example, a Dynapar series H25 encoder is used which provides 1 to 1024 pulses per revolution. The exposure control of the camera of the camera assembly 20 is automatically controlled by way of the IPS 30 based on the speed input signals from the encoder 60. As the web 50 speeds up, the exposure time of the camera is increased. As the web 50 slows down, the exposure time of the camera is decreased. The exposure time of the camera must be shorter than the line time of the web, and is initially set for the fastest line time such that the exposure setting is automatically adjusted to accommodate any slower line times the web 50 may be operating at.

The light assembly 70 includes mounting brackets to allow adjustment of the height and angle of the light provided to the web 50. The light assembly 70 further includes a light sensor and a ballast such that a constant light intensity is automatically maintained. A user can adjust the light intensity via the IPS 30. The light assembly 70 utilizes a light source such as a fiber optic light source or a TIR halogen type light source. In a particular example, the light assembly 70 utilizes an IRIDIS 400 W metal halide light source in an aluminum light housing. Metal halide lights operate at a high frequency and therefore can be used to accommodate fast line speeds. The metal halide lights are particularly useful for the inspection of non-woven textiles and films.

Figure 2A:
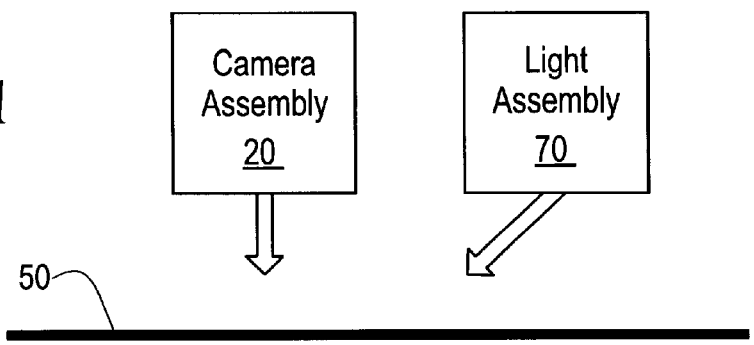
FIG. 2A is a block diagram of the web inspection system utilizing diffuse lighting.

Referring now to FIG. 2A, the web inspection system is shown wherein the camera assembly 20 is disposed generally perpendicular to the web of material 50 and the light produced by light assembly 70 is diffuse and provided at an angle onto the web 50. The web 50 is recorded by the camera assembly 20 as the web passes directly beneath the camera assembly 20. This orientation of the camera assembly 20 and the light assembly 70 with respect to the web 50 is most useful for detecting surface coloration caused by spots and large holes and for detecting large deformations such as rips and tears.

Figure 2B:
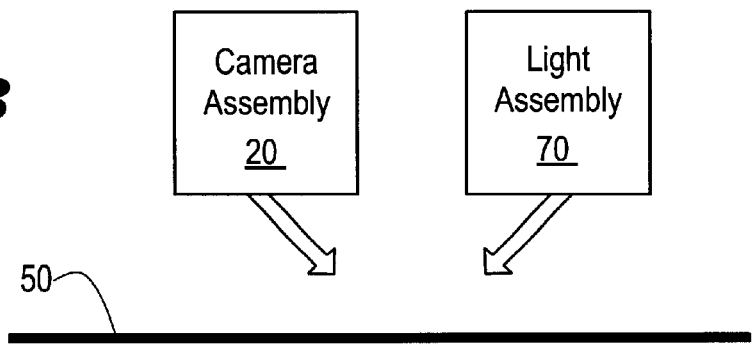
FIG. 2B is a block diagram of the web inspection system utilizing specular lighting.

FIG. 2B shows an orientation wherein camera assembly 20 is disposed at an angle with respect to the web 50 as is the light assembly 70. Light assembly 70 in this instance is providing specular lighting. This orientation is most useful for detecting texture changes caused by bumps and roller impressions.

Figure 2C:
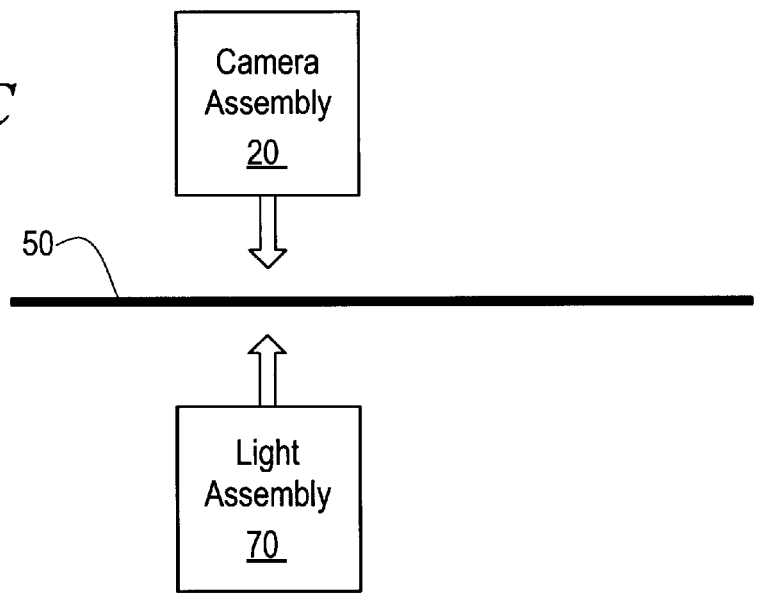
FIG. 2C is a block diagram of the web inspection system utilizing transmissive lighting.

Referring now to FIG. 2C, the camera assembly 20 is shown generally perpendicular to the web 50 while light assembly 70 is disposed subjacent the web 50. In this instance light assembly 70 is providing transmissive lighting. This arrangement is best suited for detecting holes, texture defects and gels.

Referring back to FIG. 1, the web inspection system 10 allows for inspection of a wide variety of materials such as paper, film, metals and textiles. In a particular embodiment the web inspection system can view a ten meter wide web of material traveling at a line speed of 1,500 meters per minute, and can detect defects as small as 25 microns. The analysis by the system takes into account and compensates for variations in lighting, machine speed, lens effects and defect contrast, size, density and orientation that may be difficult to otherwise detect.

Operators/inspectors view continuous live video images of the web showing all the web's characteristics, including web defects, present at that point in the operation. The system can also playback the images that have been captured. The system economically detects and classifies a variety of defects from quickly moving webs to minimize scrap, downtime and to enhance quality. The system is a complete, portable web inspection analysis system and is readily integrated with an existing web process to provide an accurate indication of web quality. The web inspection system acquires and digitally records dynamic defect data from the web in real time. The system steps through recorded sequences to provide instant feedback on resolution and lighting. When installed as part of a production machine, the system detects and classifies defects in real-time at production speeds. By setting the cameras at an appropriate scale and resolution, web defects as small as 25 microns can be detected.

Having described preferred embodiments of the invention, it will now become apparent to those skilled in the art that other embodiments incorporating these concepts may be used. Accordingly, it is submitted that the invention should not be limited to the described embodiments but rather should be limited only by the scope and spirit of the appended claims.

We claim:

1. A web inspection system comprising:

a camera assembly disposed proximate a moving web of material, said camera assembly providing a continuous sequence of real time images of the web as the web passes by said camera assembly;

an image processing system in electrical communication with said camera assembly, the image processing system including a storage element for storage of the continuous sequence of images of the moving web of material;

a light assembly for providing illumination to said web, said light assembly comprising a light source with a light sensor and a ballast in communication with said light source, such that a constant light intensity is automatically maintained, said light assembly in electrical communication with said image processing system; and a video display in electrical communication with said image processing system, said video display operative to display the continuous sequence of images of the web.

2. The web inspection system of claim 1 wherein said storage element comprises a disk drive.

3. The web inspection system of claim 1 wherein said storage element comprises a video disk drive.

4. The web inspection system of claim 1 further comprising an encoder disposed adjacent said web, said encoder in electrical communication with said image processing system.

5. The web inspection system of claim 1 wherein said camera assembly comprises:

an enclosure;

a camera disposed within said enclosure; and an adjustable mount for securing said camera and said enclosure in a stable position.

6. The web inspection system of claim 5 wherein said camera assembly further comprises an encoder interface in electrical communication with said image processing system.

7. The web inspection system of claim 5 wherein said camera assembly further comprises a light control interface in electrical communication with said image processing system.

8. The web inspection system of claim 5 wherein said camera is selected from the group consisting of a linear array camera, an area camera and a TDI camera.

9. The web inspection system of claim 1, wherein said light assembly comprises:

an enclosure; disposed about said light source a mounting bracket for securing said enclosure and said light source in a stable position.

10. The web inspection system of claim 1 wherein said light source is selected from the group consisting of a metal halide light and a fiber optic light.

11. The web inspection system of claim 1 wherein said camera assembly is disposed generally perpendicular to said web.

12. The web inspection system of claim 1 wherein said camera assembly is disposed obliquely with respect to said web.

13. The web inspection system of claim 9 wherein said light source is disposed subjacent with respect to said web.

14. The web inspection system of claim 9 wherein said light source is disposed obliquely with respect to said web.

15. The web inspection system of claim 1 wherein said video display is operative to display the continuous sequence of images of the web as said camera assembly is providing the continuous sequence of images of the web.

16. The web inspection system of claim 1 wherein said video display is operative to display the continuous sequence of images of the web at a later time than a time said camera assembly is providing the continuous sequence of images of the web.

17. The web inspection system of claim 1 wherein said web inspection system is operative to display the continuous sequence of images of the web at a slower speed than a speed of the moving web.

18. The web inspection system of claim 1 wherein the web of material is selected from the group consisting of paper, film, metal and textile.

19. The web inspection system of claim 1 wherein the web of moving material travels at a speed of up to approximately 1500 meters/second.

20. The web inspection system of claim 1 wherein said inspection system is operative to detect defects greater than approximately twenty five microns.

21. The web inspection system of claim 1 wherein said image processing system is operative to build an image database of defect images detected.

22. The web inspection system of claim 1 wherein said image processing system is operative to identify and classify detected defects.

23. The web inspection system of claim 1 wherein said image processing system is operative to sort and display detected defects.

24. The web inspection system of claim 1 wherein said continuous sequence of real time images are provided as digital images.

25. The web inspection system of claim 1 wherein said inspection system is operative to view a web up to approximately ten meters wide.

* * * * *